United States Patent
Kubota et al.

(10) Patent No.: US 6,875,881 B2
(45) Date of Patent: Apr. 5, 2005

(54) PREPARATION OF BRANCHED TETRASILOXANE

(75) Inventors: Yasufumi Kubota, Niigata-ken (JP); Tohru Kubota, Niigata-ken (JP); Satoshi Onai, Gunma-ken (JP); Koji Sakuta, Gunma-ken (JP); Akira Yamamoto, Gunma-ken (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 10/854,197

(22) Filed: May 27, 2004

(65) Prior Publication Data

US 2004/0242912 A1 Dec. 2, 2004

(30) Foreign Application Priority Data

May 30, 2003 (JP) ........................................ 2003-153931

(51) Int. Cl.$^7$ .................................................. C07F 7/08
(52) U.S. Cl. ........................ 556/456; 556/451; 556/453; 556/462
(58) Field of Search ................................ 556/451, 453, 556/456, 462

(56) References Cited

FOREIGN PATENT DOCUMENTS

| EP | 1 213 006 A1 | 6/2002 |
|----|--------------|--------|
| JP | 11-217389 A | 8/1999 |
| JP | 2002-68930 A | 3/2002 |
| WO | 2001/15658 A1 | 3/2001 |

OTHER PUBLICATIONS

M. G. Voronkov et al.; "Cleavage of the SiOSi Grouping by Tetrachlorosilane and Organylchlorosilanes"; Doklady Akademii Nauk SSSR, vol. 227, (1976) No. 2, pp. 362–265.

Isao Hasegawa et al.; "Treatment of alkyltriethoxysilances with Amberlyst 15 cation–exchange resin in the presence of hexamethyloxane"; Journal of Organometallic Chemistry, vol. 340 (1988) pp. 31–36.

*Primary Examiner*—Samuel Barts
(74) *Attorney, Agent, or Firm*—Birch, Stewart, Kolasch & Birch, LLP

(57) ABSTRACT

A branched tetrasiloxane is prepared by preforming a liquid mixture of a disiloxane compound, an alcohol and an acid catalyst, adding a trialkoxysilane compound to the mixture for reaction, and adding water to the reaction mixture for co-hydrolysis, thereby forming a branched tetrasiloxane. The method is capable of preparing a branched tetrasiloxane, especially methyltris(trimethylsiloxy)silane having a sufficiently high purity to use as cosmetic oil in good yields.

5 Claims, No Drawings

PREPARATION OF BRANCHED TETRASILOXANE

This Nonprovisional application claims priority under 35 U.S.C. § 119(a) on Patent Application No(s). 2003-153931 filed in Japan on May 30, 2003, the entire contents of which are hereby incorporated by reference.

TECHNICAL FIELD

This invention relates to a method for preparing branched tetrasiloxanes such as methyltris(trimethylsiloxy)-silane, useful as siloxane industrial oil, cosmetic oil and detergents.

BACKGROUND ART

Branched tetrasiloxanes as typified by methyltris(trimethylsiloxy)silane are used as industrial oil, cosmetic oil and detergents. For the tetrasiloxane used as cosmetic oil among other applications, high purity is a critical requirement. Specifically, it is desired to reduce the content of impurity ingredients of one silicon atom below 0.1% by weight because they are highly irritant to the skin. It is also desired to minimize the content of linear and cyclic compounds of two or three silicon atoms because they are also highly irritant to the skin.

It is thus desirable that the methyltris(trimethylsiloxy)silane used as cosmetic oil be highly pure with a minimized content of low-boiling silicon-containing ingredients.

Several methods for the preparation of methyltris(trimethylsiloxy)silane are known in the art.
(1) Co-hydrolysis of methyltrichlorosilane and trimethylchlorosilane in the presence of methanol. See International Patent Publication 2001/15658 and JP-A 2002-68930.
(2) Reaction of methyltrichlorosilane with hexamethyldisiloxane in the presence of a perchloric acid catalyst. See Dokl. Akad. Nauk., SSSR, 1976, 227, 362–365.
(3) Reaction of methyltriethoxysilane with hexamethyldisiloxane in the presence of an acidic ion-exchange resin. See J. Organomet. Chem., 1988, 340, 31–36.
(4) Reaction of methyltrialkoxysilane with hexamethyldisiloxane in the presence of a carboxylic acid and an acid catalyst. See JP-A 11-217389.
(5) Addition of conc. sulfuric acid to methyltrimethoxysilane, hexamethyldisiloxane and methanol, followed by dropwise addition of a mixture of water and methanol. See International Patent Publication 2001/15658 and JP-A 2002-68930.

These methods, however, have drawbacks. Method (1) needs a large amount of water and have very low yields due to a low selectivity of reaction. Method (2) is inadequate from an industrial aspect since the catalyst used is perchloric acid which is awkward to handle. Method (3) must use a large excess of hexamethyldisiloxane in order to increase the rate of reaction. Nevertheless, a large amount of the reaction intermediate, 1,1,1,3,5,5,5-heptamethyl-3-ethoxytrisiloxane is left behind. The method is thus unsuitable for obtaining methyltris(trimethylsiloxy)silane in high purity form. In Method (4), there are produced not only the desired methyltris(trimethylsiloxy)silane, but also a noticeable amount of a by-product having a similar boiling point, 1,1,1,3,5,5,5-heptamethyl-3-methoxytrisiloxane. Although the yield at the reaction solution stage is 82%, it is estimated that the yield upon isolation becomes substantially lower where distillation is effected to obtain highly pure methyltris(trimethylsiloxy)silane. Method (5) produces highly pure methyltris(trimethylsiloxy)silane, but is unsatisfactory because of a yield as low as 70%.

None of prior art methods are capable of preparing branched tetrasiloxanes in good yields, especially methyltris(trimethylsiloxy)silane of a sufficiently high purity to use as cosmetic oil in good yields.

SUMMARY OF THE INVENTION

In contrast to the prior art method of adding conc. sulfuric acid to a mixture of methyltrimethoxysilane, hexamethyldisiloxane and methanol, followed by dropwise addition of a mixture of water and methanol for co-hydrolysis, surprisingly, the inventor has found that a high purity branched tetrasiloxane can be produced in high yields by adding a trialkoxysilane compound to a mixture of a disiloxane compound, an alcohol and an acid catalyst for reaction and adding water thereto for co-hydrolysis.

The present invention provides a method for preparing a branched tetrasiloxane, comprising the steps of:

preforming a liquid mixture of a disiloxane compound having the general formula (1):

$$R^1{}_3SiOSiR^1{}_3 \qquad (1)$$

wherein $R^1$ is hydrogen or a substituted or unsubstituted monovalent hydrocarbon group of 1 to 20 carbon atoms, an alcohol and an acid catalyst, adding a trialkoxysilane compound having the general formula (2):

$$R^2Si(OR^3)_3 \qquad (2)$$

wherein $R^2$ and $R^3$ each are a substituted or unsubstituted monovalent hydrocarbon group of 1 to 20 carbon atoms to the mixture and effecting reaction, and adding water to the reaction mixture to effect co-hydrolysis, thereby forming a branched tetrasiloxane having the general formula (3):

$$R^2Si(OSiR^1{}_3)_3 \qquad (3)$$

wherein $R^1$ and $R^2$ are as defined above.

DESCRIPTION OF THE PREFERRED EMBODIMENTS

The method for preparing a branched tetrasiloxane according to the invention involves the steps of preforming a liquid mixture of a disiloxane compound having the general formula (1):

$$R^1{}_3SiOSiR^1{}_3 \qquad (1)$$

wherein $R^1$ is hydrogen or a substituted or unsubstituted monovalent hydrocarbon group of 1 to 20 carbon atoms, an alcohol and an acid catalyst, adding a trialkoxysilane compound having the general formula (2):

$$R^2Si(OR^3)_3 \qquad (2)$$

wherein $R^2$ and $R^3$ each are a substituted or unsubstituted monovalent hydrocarbon group of 1 to 20 carbon atoms to the mixture for reaction to take place, and adding water to the reaction mixture for co-hydrolysis.

The disiloxane compound used herein is represented by formula (1). In formula (1), $R^1$ stands for hydrogen or substituted or unsubstituted monovalent hydrocarbon groups of 1 to 20 carbon atoms, especially 1 to 6 carbon atoms, for example, hydrogen, alkyl groups such as methyl, ethyl, n-propyl, isopropyl, n-butyl, isobutyl, sec-butyl, tert-butyl, n-hexyl, n-octyl, n-decyl and n-octadecyl, cycloalkyl groups such as cyclopentyl and cyclohexyl, alkenyl groups such as vinyl and allyl, aryl groups such as phenyl and o-tolyl, and aralkyl groups such as benzyl and phenylethyl. $R^1$ groups may be the same or different.

Illustrative, non-limiting examples of the disiloxane compound having formula (1) include hexamethyldisiloxane, hexaethyldisiloxane, hexa-n-propyldisiloxane, 1,3-di-tert-butyl-1,1,3,3-tetramethyldisiloxane, 1,3-divinyl-1,1,3,3-tetramethyldisiloxane, hexaphenyldisiloxane, 1,1,3,3-tetramethyldisiloxane and 1,1,3,3-tetraisopropyldisiloxane.

In the practice of the invention, the disiloxane compound is preferably used in an amount of at least 1.5 moles per mole of the trialkoxysilane compound having formula (2). More preferably the disiloxane compound is used in an amount of 1.5 to 10 moles, and most preferably 1.5 to 4 moles. Outside the range, less amounts may result in lower yields of the branched tetrasiloxane whereas in larger amounts, no further improvement in yield is expectable and the pot yield will sometimes drop.

Examples of the alcohol used herein include methanol, ethanol, n-propanol, isopropanol, n-butanol and isobutanol. Of these, methanol, ethanol and isopropanol are preferred. In the practice of the invention, the alcohol is preferably used in an amount of 0.2 to 10 moles, more preferably 1 to 3 moles, per mole of the trialkoxysilane compound having formula (2). Outside the range, less amounts may result in lower yields of the branched tetrasiloxane whereas larger amounts may sometimes invite a drop of pot yield.

Examples of the acid catalyst used herein include sulfuric acid, hydrochloric acid, methanesulfonic acid, and trifluoromethanesulfonic acid. Of these, sulfuric acid and trifluoromethanesulfonic acid are preferred. In the practice of the invention, the acid catalyst is preferably used in an amount of 0.001 to 0.5 mole, more preferably 0.01 to 0.2 mole, per mole of the trialkoxysilane compound having formula (2). Less amounts may provide a lower rate of reaction, requiring a longer reaction time. Larger amounts may allow the reaction product, branched tetrasiloxane to take a higher molecular weight due to redistribution reaction, resulting in lower yields.

The disiloxane compound, alcohol and acid catalyst, described above, are combined to form a liquid mixture.

To the liquid mixture was added a trialkoxysilane compound of formula (2). In formula (2), $R^2$ stands for substituted or unsubstituted monovalent hydrocarbon groups of 1 to 20 carbon atoms, especially 1 to 6 carbon atoms, for example, alkyl groups such as methyl, ethyl, n-propyl, isopropyl, n-butyl, isobutyl, sec-butyl, tert-butyl, n-hexyl, n-octyl, n-decyl and n-octadecyl, cycloalkyl groups such as cyclopentyl and cyclohexyl, alkenyl groups such as vinyl and allyl, aryl groups such as phenyl and o-tolyl, aralkyl groups such as benzyl and phenylethyl, and halogen-substituted alkyl groups such as 3-chloropropyl and 3-iodopropyl.

In formula (2), $R^3$ stands for substituted or unsubstituted monovalent hydrocarbon groups of 1 to 20 carbon atoms, especially 1 to 6 carbon atoms, for example, alkyl groups such as methyl, ethyl, n-propyl, isopropyl, n-butyl, isobutyl, sec-butyl, tert-butyl, n-hexyl, n-octyl, n-decyl and n-octadecyl, and cycloalkyl groups such as cyclopentyl and cyclohexyl.

Illustrative, non-limiting examples of the trialkoxysilane compound having formula (2) include methyltrimethoxysilane, methyltriethoxysilane, methyltri-n-propoxysilane, methyltriisopropoxysilane, ethyltrimethoxysilane, ethyltriethoxysilane, ethyltri-n-propoxysilane, ethyltriisopropoxysilane, n-propyltrimethoxysilane, n-propyltriethoxysilane, n-propyltri-n-propoxysilane, n-propyltriisopropoxysilane, isopropyltrimethoxysilane, isopropyltriethoxysilane, n-butyltrimethoxysilane, n-butyltriethoxysilane, n-hexyltrimethoxysilane, n-hexyltriethoxysilane, n-octyltrimethoxysilane, n-octyltriethoxysilane, n-decyltrimethoxysilane, n-decyltriethoxysillane, n-octadecyltrimethoxysilane, n-octadecyltriethoxysilane, vinyltrimethoxysilane, vinyltriethoxysilane, vinyltri-n-propoxysilane, vinyltriisopropoxysilane, phenyltrimethoxysilane, phenyltriethoxysilane, phenyltri-n-propoxysilane, phenyltriisopropoxysilane, 3-chloropropyltrimethoxysilane, 3-chloropropyltriethoxysilane, 3-chloropropyltri-n-propoxysilane, 3-chloropropyltriisopropoxysilane, 3-iodopropyltrimethoxysilane, 3-iodopropyltriethoxysilane, 3-iodopropyltri-n-propoxysilane, and 3-iodopropyltriisopropoxysilane.

The trialkoxysilane compound may be used after it is conventionally synthesized and ordinarily purified. In one preferred embodiment, a reaction solution as synthesized from a trichlorosilane and an alcohol through de-hydrochlorination reaction is used without purification. The trichlorosilane compounds used in the synthesis of trialkoxysilane compounds are those of formula (2) wherein the alkoxysilyl groups are replaced by chloro groups, and examples thereof include methyltrichlorosilane, ethyltrichlorosilane, n-propyltrichlorosilane, isopropyltrichlorosilane, n-butyltrichlorosilane, n-hexyltrichlorosilane, n-octyltrichlorosilane, n-decyltrichlorosilane, n-octadecyltrichlorosilane, vinyltrichlorosilane, phenyltrichlorosilane, and 3-chloropropyltrichlorosilane. Examples of the alcohol to be reacted with the trichlorosilane include methanol, ethanol, n-propanol, isopropanol, n-butanol, and isobutanol, with methanol, ethanol and isopropanol being preferred. The crude trialkoxysilane compound obtained from the trichlorosilane and alcohol through de-hydrochlorination reaction, though not purified, has a relatively high purity and contains the alcohol and a trace of disiloxane as impurities. The crude trialkoxysilane compound can be used in the instant reaction without further treatment for purification as long as its purity is 50% or higher. A purity of 80% or higher is preferred, and more preferably 90% or higher.

Water is then added to the reaction mixture whereupon hydrolysis takes place. In this step, water may be used alone or in admixture with an alcohol. In the practice of the invention, water is preferably used in an amount of 1 to 50 moles, more preferably 1.5 to 20 moles, most preferably 2 to 8 moles, per mole of the trialkoxysilane compound having formula (2). Less amounts of water may result in lower yields because the reaction does not proceed to completion. With larger amounts, no further improvement in yield is expectable and the pot yield will sometimes drop. The optional alcohol added to water is used in a molar amount less than the moles of water used. Suitable alcohols include methanol, ethanol, n-propanol, isopropanol, n-butanol, and isobutanol. Preferably the alcohol used in the hydrolysis step is the same as that used together with the disiloxane compound of formula (1).

According to the invention, a trialkoxysilane compound is added to a liquid mixture of a disiloxane compound, an alcohol and an acid catalyst for effecting reaction, and water is then added to the reaction mixture for effecting co-hydrolysis. By contrast, if a trialkoxysilane compound is added to a liquid mixture of a disiloxane compound and an alcohol prior to the addition of an acid catalyst, then by-products including pentasiloxane and hexasiloxane are formed in larger amounts to eventually reduce the yield of the desired branched tetrasiloxane. The order of mixing the disiloxane compound alcohol and acid catalyst is arbitrary although it is more preferred to add the acid catalyst to a liquid mixture of the disiloxane compound and alcohol.

In this preferred procedure, the acid catalyst is desirably added to a liquid mixture of the disiloxane compound of formula (1) and the alcohol at a temperature of 0 to 100° C., more desirably 5 to 40° C. The mixture is desirably held at the temperature for 0.1 to 5 hours, more desirably 0.5 to 2 hours. Then the trialkoxysilane compound of formula (2) is desirably added to the liquid mixture at a temperature of 0 to 100° C., more desirably 5 to 70° C. The reaction time is desirably 0.5 to 8 hours, more desirably 0.5 to 3 hours. Subsequently, water is desirably added to the reaction mixture at a temperature of 1 to 100° C., more desirably 1 to 70° C. Outside the range, lower temperatures may cause the reaction mixture to coagulate due to water freezing. At higher temperatures, the once produced tetrasiloxane may convert to penta- and hexa-siloxanes through redistribution reaction, resulting in reduced yields of the branched tetrasiloxane.

The reaction may be carried out without a solvent although a solvent may be used. Suitable solvents include hydrocarbon solvents such as hexane, cyclohexane, heptane, octane, isooctane, dodecane, benzene, toluene and xylene, and ether solvents such as tetrahydrofuran and dioxane.

In the practice of the invention, the reaction mixture at the end of reaction is preferably divided into aqueous and organic layers by separatory operation whereupon the organic layer is neutralized with a basic aqueous solution such as sodium bicarbonate in water. The organic layer is then washed with water until neutral. After washing, the reaction solution may be dried over a desiccant such as anhydrous sodium sulfate or calcium chloride and then purified by distillation, or directly purified by distillation without adding a desiccant. Distillation can be done under atmospheric or reduced pressure in a conventional manner. In this way, the desired branched tetrasiloxane is obtained.

The branched tetrasiloxane thus obtained has the following formula (3):

$$R^2Si(OSiR^1{}_3)_3 \qquad (3)$$

wherein $R^1$ and $R^2$ are as defined above.

Illustrative, non-limiting examples of the branched tetrasiloxane having formula (3) include
methyltris(trimethylsiloxy)silane,
methyltris(triethylsiloxy)silane,
methyltris(dimethylvinylsiloxy)silane,
methyltris(dimethylsiloxy)silane,
ethyltris(trimethylsiloxy)silane,
ethyltris(triethylsiloxy)silane,
ethyltris(dimethylvinylsiloxy)silane,
ethyltris(dimethylsiloxy)silane,
n-propyltris(trimethylsiloxy)silane,
n-propyltris(triethylsiloxy)silane,
n-propyltris(dimethylvinylsiloxy)silane,
n-propyltris(dimethylsiloxy)silane,
vinyltris(trimethylsiloxy)silane,
vinyltris(triethylsiloxy)silane,
vinyltris(dimethylvinylsiloxy)silane,
vinyltris(dimethylsiloxy)silane,
phenyltris(trimethylsiloxy)silane,
phenyltris(triethylsiloxy)silane,
phenyltris(dimethylvinylsiloxy)silane, and
phenyltris(dimethylsiloxy)silane.

EXAMPLE

Examples of the invention are given below by way of illustration and not by way of limitation.

Example 1

A 2000-ml, four-necked glass flask was equipped with a reflux condenser, thermometer and stirrer and internally purged with nitrogen gas. The flask was charged with 649.6 g (4.0 mol) of hexamethyldisiloxane and 128.0 g (4.0 mol) of methanol and cooled in an ice water bath to an internal temperature below 10° C. To the flask maintained at an internal temperature of 5 to 10° C., 19.6 g (0.2 mol) of conc. sulfuric acid was added dropwise over 30 minutes, after which the contents were stirred for 30 minutes at the temperature. Subsequently, 272.4 g (2.0 mol) of methyltrimethoxysilane was added dropwise over 45 minutes to the flask which was maintained at an internal temperature of 5 to 10° C., after which the contents were stirred for one hour at the temperature. Then, 209.9 g (11.7 mol) of water was added dropwise over one hour at an internal temperature of 5 to 25° C. After the completion of dropwise addition, stirring was continued for 3 hours at 5 to 25° C. The resulting reaction solution was subjected to separatory operation whereby the water layer was separated off. The organic layer was washed with aqueous sodium bicarbonate and then with water. The organic layer was distilled, collecting a fraction having a boiling point of 120.0–120.5° C./12 kPa, that is, 547.5 g (1.76 mol) of methyltris(trimethylsiloxy)silane of 99.6% pure. The yield was 88.1%.

Example 2

A 1000-ml, four-necked glass flask was equipped with a reflux condenser, thermometer and stirrer and internally purged with nitrogen gas. The flask was charged with 487.2 g (3.0 mol) of hexamethyldisiloxane and 64.0 g (2.0 mol) of methanol and cooled in an ice water bath to an internal temperature below 10° C. To the flask maintained at an internal temperature of 5 to 10° C., 9.89 (0.1 mol) of conc. sulfuric acid was added dropwise over 15 minutes, after which the contents were stirred for 30 minutes at the temperature. Subsequently, 136.2 g (1.0 mol) of methyltrimethoxysilane was added dropwise over 30 minutes to the flask which was maintained at an internal temperature of 5 to 10° C., after which the contents were stirred for one hour at the temperature. Then, 105.0 g (5.83 mol) of water was added dropwise over one hour at 5 to 25° C. After the completion of dropwise addition, stirring was continued for 3 hours at 5 to 25° C. The resulting reaction solution was subjected to separatory operation whereby the water layer was separated off. The organic layer was washed with aqueous sodium bicarbonate and then with water. The organic layer was distilled, collecting a fraction having a boiling point of 120.0–120.5° C./12 kPa, that is, 279.7 g (0.9 mol) of methyltris(trimethylsiloxy)silane of 99.5% pure. The yield was 92.0%.

Example 3

A 1000-ml, four-necked glass flask was equipped with a reflux condenser, thermometer and stirrer and internally purged with nitrogen gas. The flask was charged with 324.8 g (2.0 mol) of hexamethyldisiloxane and 64.0 g (2.0 mol) of methanol and cooled in an ice water bath to an internal temperature below 10° C. To the flask maintained at an internal temperature of 5 to 10° C., 7.5 g (0.05 mol) of trifluoromethanesulfonic acid was added dropwise over 20 minutes, after which the contents were stirred for 30 minutes at the temperature. Subsequently, 136.2 g (1.0 mol) of methyltrimethoxysilane was added dropwise over 30 minutes to the flask which was maintained at an internal temperature of 5 to 10° C., after which the contents were stirred for one hour at the temperature. Then, 105.0 g (5.83 mol) of water was added dropwise over one hour at an internal temperature of 5 to 25° C. After the completion of dropwise addition, stirring was continued for 3 hours at 5 to 25° C. The resulting reaction solution was subjected to separatory operation whereby the water layer was separated off. The organic layer was washed with aqueous sodium bicarbonate and then with water. The organic layer was distilled, collecting a fraction having a boiling point of 120.0–120.5° C./12 kPa, that is, 271.9 g (0.88 mol) of methyltris(trimethylsiloxy)silane of 99.5% pure. The yield was 87.5%.

Example 4

A 2000-ml, four-necked glass flask was equipped with a reflux condenser, thermometer and stirrer and internally purged with nitrogen gas. The flask was charged with 649.6 g (4.0 mol) of hexamethyldisiloxane and 128.09 (4.0 mol) of methanol and cooled in an ice water bath to an internal temperature below 10° C. To the flask maintained at an internal temperature of 5 to 10° C., 19.6 g (0.2 mol) of conc. sulfuric acid was added dropwise over 30 minutes, after which the contents were stirred for 30 minutes at the temperature. Subsequently, 283.5 g of crude methyltrimethoxysilane, which had been synthesized from methyltrichlorosilane and methanol through dehydrochlorination reaction (neat methyltrimethoxysilane 2.0 mol), was added dropwise over 45 minutes to the flask which was maintained at an internal temperature of 5 to 10° C., after which the contents were stirred for one hour at the temperature. Then, 209.9 g (11.7 mol) of water was added dropwise over one hour at 5 to 25° C. After the completion of dropwise addition, stirring was continued for 3 hours at 5 to 25° C. The resulting reaction solution was subjected to separatory operation whereby the water layer was separated off. The organic layer was washed with aqueous sodium bicarbonate and then with water. The organic layer was distilled, collecting a fraction having a boiling point of 120.0–120.5° C./12 kPa, that is, 556.5 g (1.79 mol) of methyltris(trimethylsiloxy)silane of 99.6% pure. The yield was 89.3%.

Example 5

A 1000-ml, four-necked glass flask was equipped with a reflux condenser, thermometer and stirrer and internally purged with nitrogen gas. The flask was charged with 324.8 g (2.0 mol) of hexamethyldisiloxane and 92.2 g (2.0 mol) of ethanol and cooled in an ice water bath to an internal temperature below 10° C. To the flask maintained at an internal temperature of 5 to 10° C., 9.8 g (0.1 mol) of conc. sulfuric acid was added dropwise over 20 minutes, after which the contents were stirred for 30 minutes at the temperature. Subsequently, 136.2 g (1.0 mol) of methyltriethoxysilane was added dropwise over 30 minutes to the flask which was maintained at an internal temperature of 5 to 10° C., after which the contents were stirred for one hour at the temperature. Then, 105.0 g (5.83 mol) of water was added dropwise over one hour at 5 to 25° C. After the completion of dropwise addition, stirring was continued for 4 hours at 5 to 25° C. The resulting reaction solution was subjected to separatory operation whereby the water layer was separated off. The organic layer was washed with aqueous sodium bicarbonate and then with water. The organic layer was distilled, collecting a fraction having a boiling point of 120.0–120.5° C./12 kPa, that is, 273.4 g (0.88 mol) of methyltris(trimethylsiloxy)silane of 99.4% pure. The yield was 88.0%.

Example 6

A 2000-ml, four-necked glass flask was equipped with a reflux condenser, thermometer and stirrer and internally purged with nitrogen gas. The flask was charged with 649.6 g (4.0 mol) of hexamethyldisiloxane and 128.0 g (4.0 mol) of methanol and cooled in an ice water bath to an internal temperature below 10° C. To the flask maintained at an internal temperature of 5 to 10° C., 19.6 g (0.2 mol) of conc. sulfuric acid was added dropwise over 30 minutes, after which the contents were stirred for 30 minutes at the temperature. Subsequently, 328.6 g (2.0 mol) of n-propyltrimethoxysilane was added dropwise over 45 minutes to the flask which was maintained at an internal temperature of 5 to 10° C., after which the contents were stirred for one hour at the temperature. Then, 144.0 g (8.0 mol) of water was added dropwise over one hour at 5 to 25° C. After the completion of dropwise addition, stirring was continued for 3 hours at 5 to 25° C. The resulting reaction solution was subjected to separatory operation whereby the water layer was separated off. The organic layer was washed with aqueous sodium bicarbonate and then with water. The organic layer was distilled, collecting a fraction having a boiling point of 70.0–70.5° C./0.5 kPa, that is, 597.7 g (1.76 mol) of n-propyltris(trimethylsiloxy)silane of 99.8% pure. The yield was 88.2%.

Example 7

A 2000-ml, four-necked glass flask was equipped with a reflux condenser, thermometer and stirrer and internally purged with nitrogen gas. The flask was charged with 649.6 g (4.0 mol) of hexamethyldisiloxane and 128.0 g (4.0 mol) of methanol and cooled in an ice water bath to an internal temperature below 10° C. To the flask maintained at an internal temperature of 5 to 10° C., 19.6 g (0.2 mol) of conc. sulfuric acid was added dropwise over 30 minutes, after which the contents were stirred for 30 minutes at the temperature. Subsequently, 412.0 g (2.0 mol) of n-hexyltrimethoxysilane was added dropwise over 45 minutes to the flask which was maintained at an internal temperature of 5 to 10° C., after which the contents were stirred for one hour at the temperature. Then, 144.0 g (8.0 mol) of water was added dropwise over one hour at 5 to 25° C. After the completion of dropwise addition, stirring was continued for 5 hours at 5 to 25° C. The resulting reaction solution was subjected to separatory operation whereby the water layer was separated off. The organic layer was washed with aqueous sodium bicarbonate and then with water. The organic layer was distilled, collecting a fraction having a boiling point of 113.5–114.5° C./1.0 kPa, that is, 646.0 g (1.7 mol) of n-hexyltris(trimethylsiloxy)silane of 99.5% pure. The yield was 85.0%.

Example 8

A 2000-ml, four-necked glass flask was equipped with a reflux condenser, thermometer and stirrer and internally purged with nitrogen gas. The flask was charged with 649.6 g (4.0 mol) of hexamethyldisiloxane and 128.0 g (4.0 mol) of methanol and cooled in an ice water bath to an internal temperature below 10° C. To the flask maintained at an internal temperature of 5 to 10° C., 19.6 g (0.2 mol) of conc. sulfuric acid was added dropwise over 30 minutes, after which the contents were stirred for 30 minutes at the temperature. Subsequently, 525.0 g (2.0 mol) of n-decyltrimethoxysilane was added dropwise over 45 minutes to the flask which was maintained at an internal temperature of 5 to 10° C., after which the contents were stirred for one hour at the temperature. Then, 144.0 g (8.0 mol) of water was added dropwise over one hour at an internal temperature of 5 to 25° C. After the completion of dropwise addition, stirring was continued for 7 hours at 5 to 25° C. The resulting reaction solution was subjected to separatory operation whereby the water layer was separated off. The organic layer was washed with aqueous sodium bicarbonate and then with water. The organic layer was distilled, collecting a fraction having a boiling point of 151.0–153.0° C./0.7 kPa, that is, 706.3 g (1.62 mol) of n-decyltris(trimethylsiloxy)silane of 98.5% pure. The yield was 81.0%.

Comparative Example

A 1000-ml, four-necked glass flask was equipped with a reflux condenser, thermometer and stirrer and internally purged with nitrogen gas. The flask was charged with 136.2 g (1.0 mol) of methyltrimethoxysilane, 324.8 g (2.0 mol) of hexamethyldisiloxane and 64.0 g (2.0 mol) of methanol and cooled in an ice water bath to an internal temperature below 10° C. To the flask maintained at an internal temperature of 5 to 10° C., 9.8 g (0.1 mol) of conc. sulfuric acid was added dropwise over 15 minutes, after which the contents were stirred for 30 minutes at the temperature. Subsequently, 105.0 g (5.83 mol) of water was added dropwise over one hour at 5 to 25° C. After the completion of dropwise addition, stirring was continued for 3 hours at 5 to 25° C. The resulting reaction solution was subjected to separatory operation whereby the water layer was separated off. The organic layer was washed with aqueous sodium bicarbonate and then with water. The organic layer was distilled, collecting a fraction having a boiling point of 120.0–120.5° C./12 kPa, that is, 225.3 g (0.73 mol) of methyltris(trimethylsiloxy)silane of 99.51 pure. The yield was 72.5%.

The method of the invention is capable of preparing branched tetrasiloxanes, especially methyltris(trimethylsiloxy)silane of a sufficiently high purity to use as cosmetic oil in good yields, and thus useful in the industry.

Japanese Patent Application No. 2003-153931 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

What is claimed is:

1. A method for preparing a branched tetrasiloxane, comprising the steps of:

preforming a liquid mixture of a disiloxane compound having the general formula (1):

$$R^1_3SiOSiR^1_3 \qquad (1)$$

wherein $R^1$ is hydrogen or a substituted or unsubstituted monovalent hydrocarbon group of 1 to 20 carbon atoms, an alcohol and an acid catalyst, adding a trialkoxysilane compound having the general formula (2):

$$R^2Si(OR^3)_3 \qquad (2)$$

wherein $R^2$ and $R^3$ each are a substituted or unsubstituted monovalent hydrocarbon group of 1 to 20 carbon atoms to the mixture and effecting reaction, and adding water to the reaction mixture to effect co-hydrolysis, thereby forming a branched tetrasiloxane having the general formula (3):

$$R^2Si(OSiR^1_3)_3 \qquad (3)$$

wherein $R^1$ and $R^2$ are as defined above.

2. The method of claim 1, wherein the disiloxane compound having formula (1) is hexamethyldisiloxane.

3. The method of claim 1, wherein the trialkoxysilane compound having formula (2) is a methyltrialkoxysilane.

4. The method of claim 1, wherein the disiloxane compound having formula (1) is hexamethyldisiloxane, the trialkoxysilane compound having formula (2) is a methyltrialkoxysilane, and the branched tetrasiloxane having formula (3) is methyltris(trimethylsiloxy)silane.

5. The method of claim 1, wherein the acid catalyst is sulfuric acid or trifluoromethanesulfonic acid.

* * * * *